(12) United States Patent
Cohen

(10) Patent No.: US 7,214,063 B2
(45) Date of Patent: May 8, 2007

(54) IMPLANT SYSTEM PARTICULARLY USEFUL FOR FIXING DENTAL PROSTHESES TO BONE

(76) Inventor: Yechiel Cohen, 4 Rotem Street P.O. Box 8436, Carmiel (IL) 21861

( * ) Notice: Subject to any disclaimer, the term of this patent is extended or adjusted under 35 U.S.C. 154(b) by 0 days.

(21) Appl. No.: 11/171,386

(22) Filed: Jul. 1, 2005

(65) Prior Publication Data

US 2006/0024644 A1    Feb. 2, 2006

(30) Foreign Application Priority Data

Jul. 29, 2004    (IL)    ......... 163284

(51) Int. Cl.
*A61C 8/00*    (2006.01)
(52) U.S. Cl. .................. 433/174; 433/173; 433/175
(58) Field of Classification Search ......... 433/172–174
See application file for complete search history.

(56) References Cited

U.S. PATENT DOCUMENTS

| | | | |
|---|---|---|---|
| 3,732,621 A * | 5/1973 | Bostrom ............... 433/174 |
| 4,713,004 A * | 12/1987 | Linkow et al. ......... 433/174 |
| 4,780,080 A | 10/1988 | Haris |
| 4,793,808 A * | 12/1988 | Kirsch ............... 433/173 |
| 4,832,601 A * | 5/1989 | Linden ............... 433/173 |
| 4,842,518 A * | 6/1989 | Linkow et al. ......... 433/174 |
| 4,932,868 A * | 6/1990 | Linkow et al. ......... 433/174 |
| 4,993,950 A * | 2/1991 | Mensor, Jr. ........... 433/173 |
| 5,015,186 A | 5/1991 | Detsch |
| 5,116,225 A | 5/1992 | Riera |
| 5,133,662 A * | 7/1992 | Metcalfe ............... 433/169 |
| 5,178,539 A * | 1/1993 | Peltier et al. ......... 433/173 |
| 5,219,286 A * | 6/1993 | Hader ................ 433/172 |
| 5,417,570 A * | 5/1995 | Zuest et al. ........... 433/177 |
| 5,480,304 A * | 1/1996 | Nardi ................ 433/172 |
| 5,516,288 A * | 5/1996 | Sichler et al. ......... 433/173 |
| 5,520,540 A * | 5/1996 | Nardi et al. .......... 433/172 |
| 5,564,922 A * | 10/1996 | Rosa et al. ........... 433/173 |
| 5,584,695 A * | 12/1996 | Lal Sachdeva et al. ... 433/173 |
| RE35,784 E * | 5/1998 | Linkow et al. ......... 433/174 |
| 5,791,899 A * | 8/1998 | Sachdeva et al. ....... 433/173 |
| 5,873,721 A | 2/1999 | Willoughby |
| 5,947,734 A * | 9/1999 | Hanel ................ 433/173 |
| 6,241,523 B1 * | 6/2001 | Nardi ................ 433/172 |
| 6,273,720 B1 * | 8/2001 | Spalten .............. 433/173 |
| 6,358,052 B1 | 3/2002 | Lustig et al. |

* cited by examiner

*Primary Examiner*—Cris L. Rodriguez
*Assistant Examiner*—Patrick J. Kilkenny

(57) ABSTRACT

An implant system includes: an implant for implanting into a bone; an abutment to serve as a support for fixing a prosthesis to the bone; and a pivotal coupling between the implant and the abutment to permit, after the implant has been implanted into the bone, precise angulation in all directions of the abutment with respect to the implant before the abutment is fixed at the desired precise angulation with respect to the implant. Preferably, the pivotal coupling includes a ball-and-socket having complementary shaped contacting surfaces which are uneven to temporarily hold them in a direct pivoted position before permanently fixing them.

11 Claims, 5 Drawing Sheets

IMPLANT SYSTEM PARTICULARLY USEFUL FOR FIXING DENTAL PROSTHESES TO BONE

FIELD AND BACKGROUND OF THE INVENTION

The present invention relates to implant systems for fixing various types of prostheses to bone. The invention is particularly useful for fixing a dental prosthesis to the lower or upper jawbone, and is therefore described below with respect to such an application, but it will be appreciated that the invention can be used in many other applications.

Implant systems are fast becoming an accepted mode for tooth replacement and/or for anchoring other types of dental prostheses to a jawbone. Such implant systems generally include an implant constructed for implanting into the bone, and an abutment constructed to serve as a support for fixing a prosthesis to the bone. A critical factor in a successful implant is the precise angulation of the abutment, which, among other factors, affects the ability of the resulting prosthesis to absorb shocks and distribute occlusal stresses to the bone/implant interface. A large number of implant systems have been developed to improve this ability, but efforts are continually being made to provide improved implant systems in this respect.

OBJECT AND BRIEF SUMMARY OF THE PRESENT INVENTION

An object of the present invention is to provide an implant system improving the ability of the resulting prosthesis to absorb shocks and distribute occlusal stresses.

According to one aspect of the present invention, there is provided an implant system, comprising: an implant constructed for implanting into a bone; an abutment constructed to serve as a support for fixing a prosthesis to the bone; and a pivotal coupling between the implant and the abutment to permit, after the implant has been implanted into the bone, precise angulation in all directions of the abutment with respect to the implant before the abutment is fixed at the desired precise angulation with respect to the implant.

It will thus be seen that such an implant system permits, even after the implant has been anchored into the bone, the abutment to be precisely angulated to its optimum position with respect to the implant before fixing the abutment to the implant.

According to further features in the described preferred embodiments, the pivotal coupling includes a ball-and-socket coupling. In one described embodiment, the ball-and-socket coupling includes complementary shaped contacting surfaces which are uneven to temporarily hold the ball-and-socket coupling in a desired pivoted position before permanently fixing the coupling in such position. In the described preferred embodiments, the ball-and-socket coupling is fixed in the desired pivotal position by an adhesive or by welding. Such an implant system may also include a shock absorber between the abutment and implant.

According to another aspect of the present invention, there is provided an implant system comprising: an implant constructed for implanting into a bone; an abutment constructed to serve as a support for fixing a prosthesis to the bone; and a shock absorber between the abutment and implant.

As will be described more particularly below, the shock absorber better enables the implant system to absorb shocks and distribute occlusal stresses to the bone/implant interface more evenly than, e.g., metal-to-metal, ceramic-to-ceramic, or ceramic-to-metal implant components.

According to further features in one described preferred embodiment, the implant is formed with a threaded bore; the implant system further comprises a fixation screw having one end threaded into the bore and an opposite end fixed within the abutment; and the shock absorber is of annular configuration and encloses the fixation screw.

Further features and advantages of the invention will be apparent from the description below.

BRIEF DESCRIPTION OF THE DRAWINGS

The invention is herein described, by way of example only, with reference to the accompanying drawings, wherein.

Figure 1:
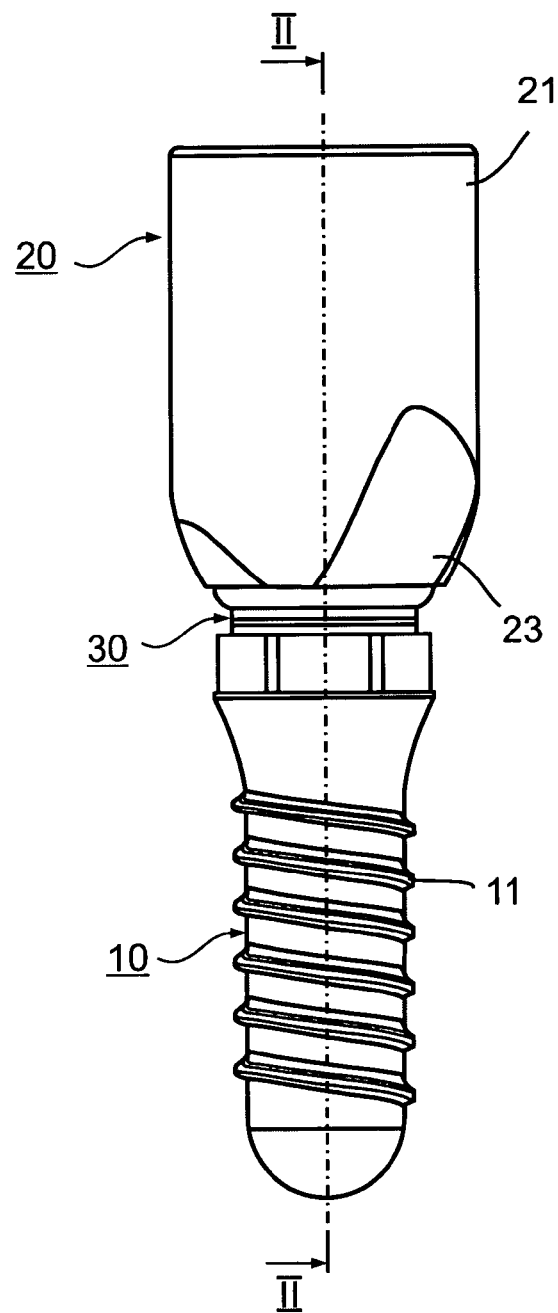
FIG. 1 is a side elevational view illustrating one form of implant system constructed in accordance with the present invention.
Figure 2:
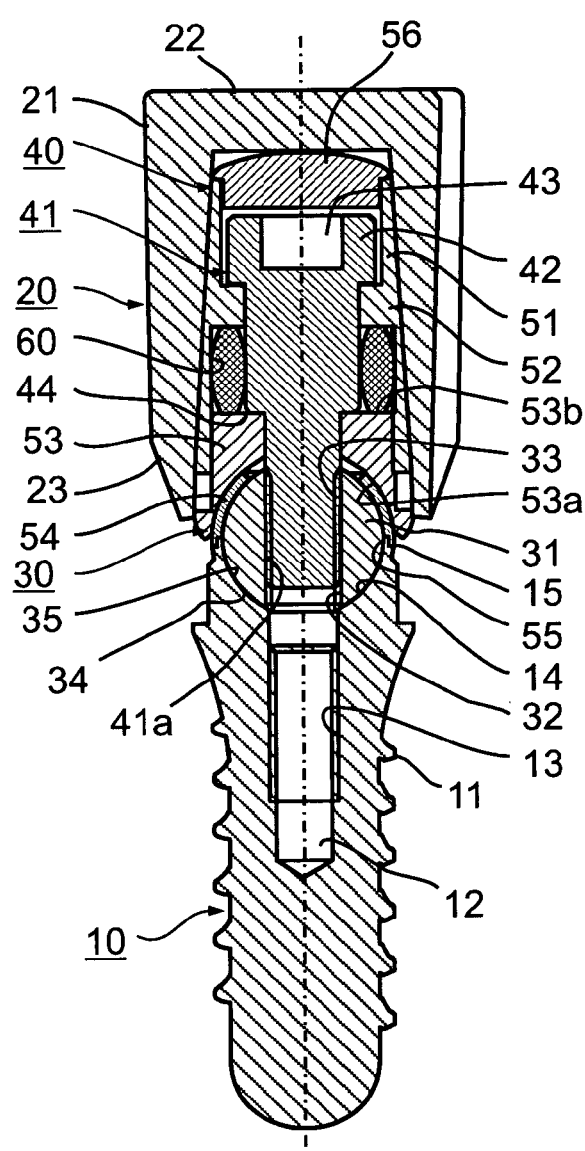
FIG. 2 is a longitudinal sectional view of FIG. 1.
Figure 3:
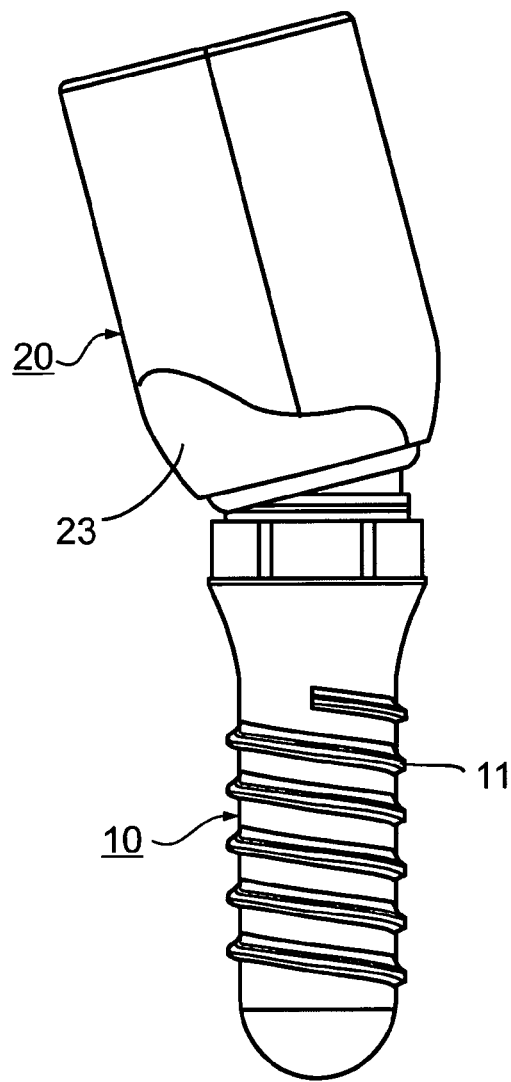
FIGS. 3 and 4 are views, corresponding to those of FIGS. 1 and 2, but showing the abutment in a pivoted position with respect to the implant.
Figure 4:
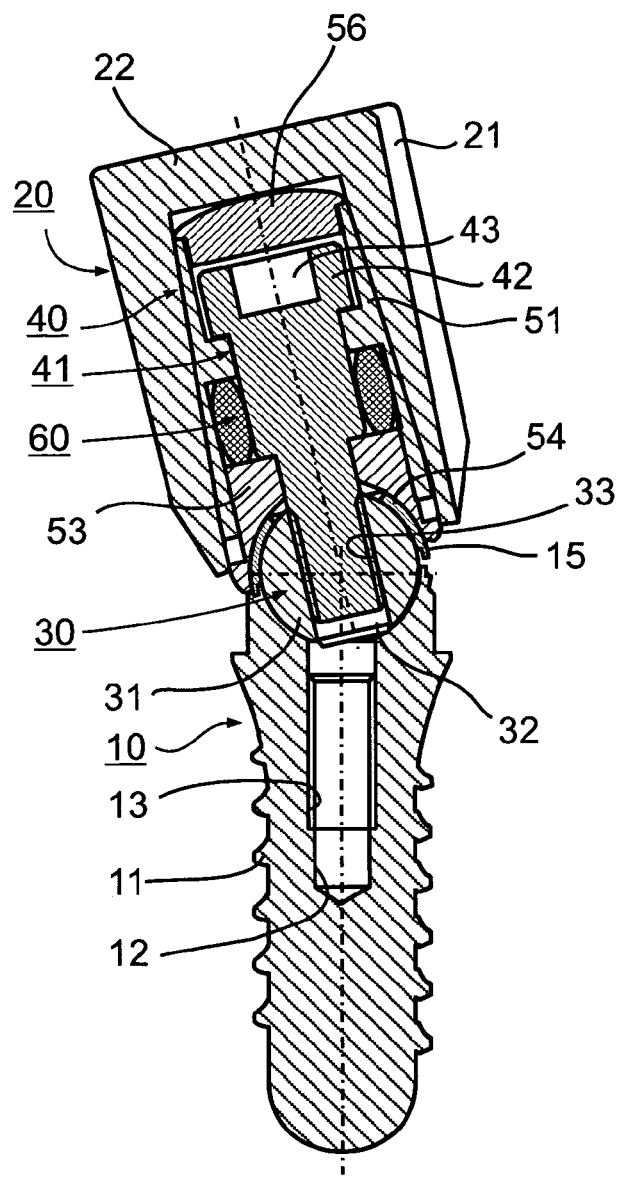
Figure 5:
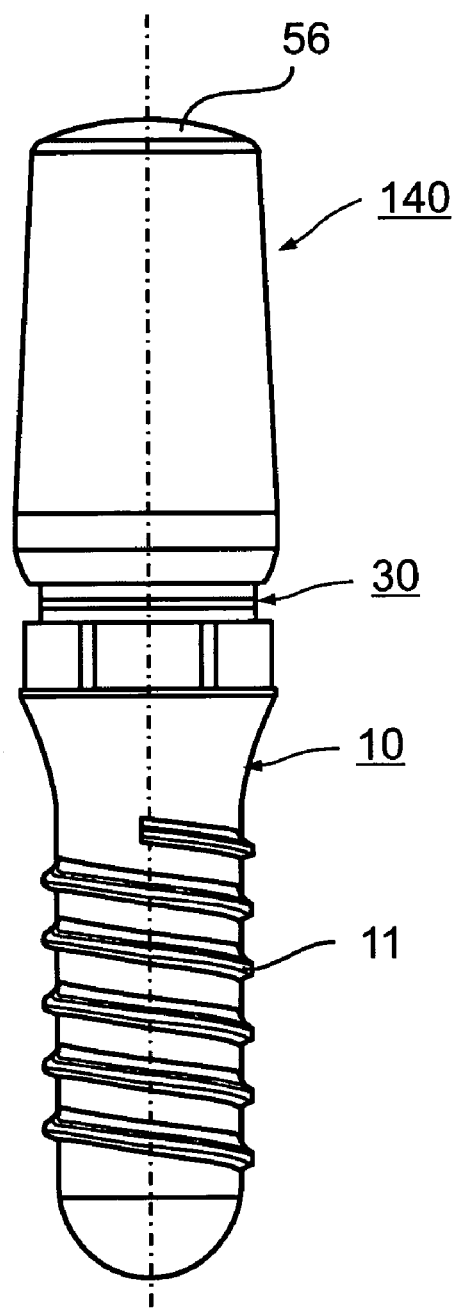
FIGS. 5–8 are views corresponding to those of FIGS. 1–4, respectively, of another implant system constructed in accordance with the present invention.
Figure 6:
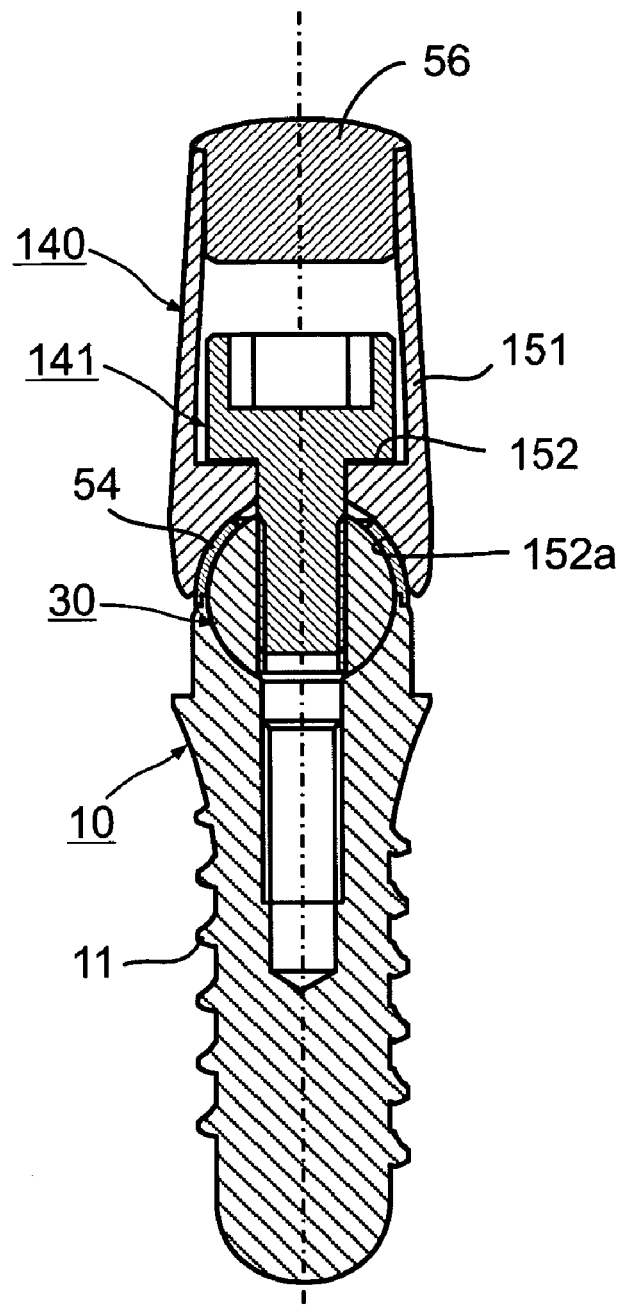
Figure 7:
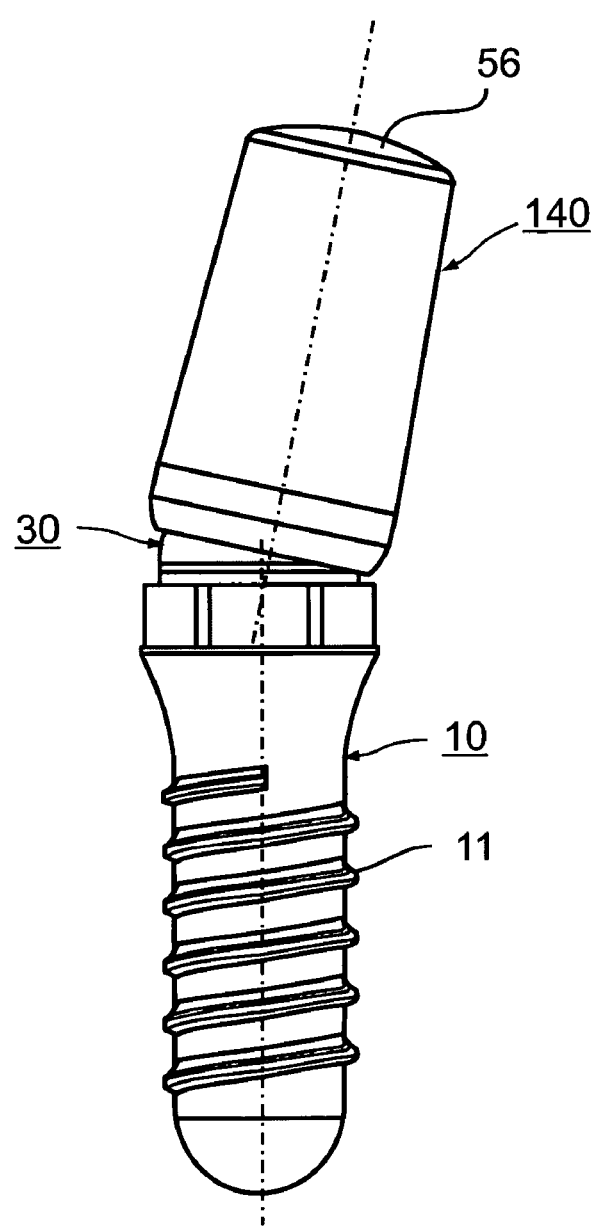
Figure 8:
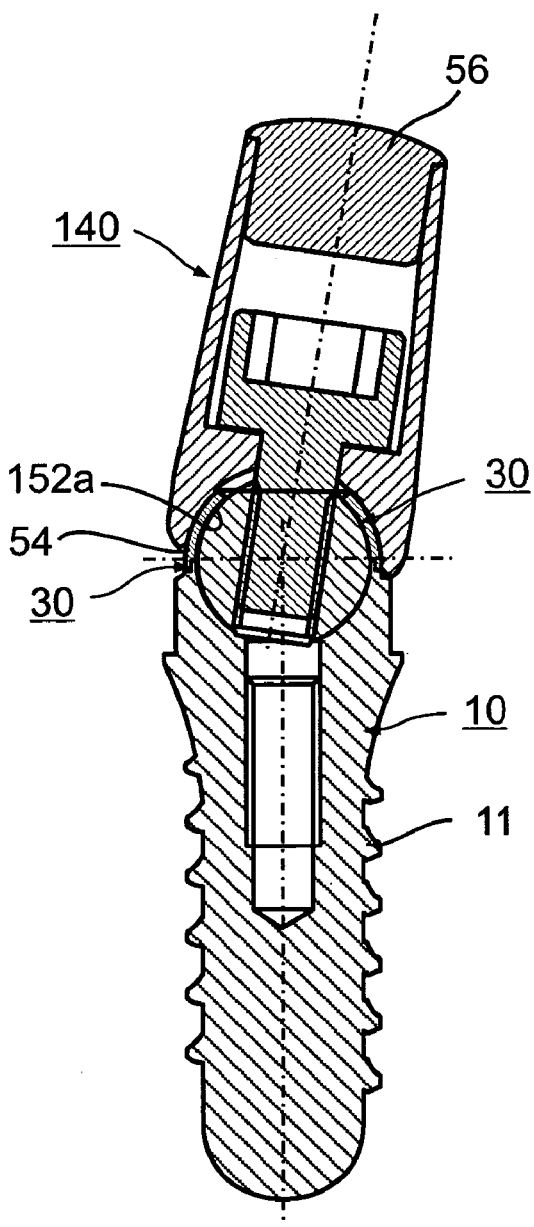

It is to be understood that the foregoing drawings, and the description below, are provided primarily for purposes of facilitating understanding the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

The Implant System of FIGS. 1–4

The implant system illustrated in FIGS. 1–4 includes an implant, generally designated 10, constructed for implanting into a bone; a prosthesis, generally designated 20 (an artificial tooth in this case) to be fixed to the implant; and an abutment, generally designated 40, serving as a support for fixing the prosthesis to the bone. The illustrated implant system further includes a pivotal coupling, generally designated 30, between the implant 10 and the abutment 40, to permit angulation in all directions of the abutment with respect to the implant after the implant has been implanted into the bone and before the prosthesis has been applied. As described more particularly below the illustrated constructions enables optimum angulation of the abutment before it is fixed with respect to the implant and before the prosthesis is fixed to the abutment.

Abutment 40 in the illustrated implant system includes a fixation screw 41, for fixing the abutment to the pivotal coupling 30, and a plurality of internal elements, identified by reference numerals starting with 50, within the abutment.

As will be described more particularly below, one of the internal elements within abutment 40 is a shock absorber 60 effective to absorb shocks and to distribute occlusal stresses to the bone/implant interface.

Implant 10 is of a solid cylindrical or conical configuration. It is formed with external threads 11 for fixing, by threading, the implant into a bore formed in the jawbone to receive the implant. The illustrated implant 10 is further formed with an axial bore 12 at its upper end, terminating substantially midway of its length. Bore 12 is threaded, as shown at 13, to enable the implant in some cases to receive fixation screw 41 of abutment 40. In the embodiment of FIGS. 1–4 (as well as in the embodiment of FIGS. 5–8), bore 12 is not actually used for receiving the fixation screw; but in the embodiment of FIGS. 9 and 10, as will be described more particularly below, bore 12 is used to receive the fixation screw for fixing the abutment to the implant.

The upper surface 14 of implant 10 is of a semi-spherical shaped configuration and serves as the socket for receiving the ball 31 of the pivotal coupling 30. The outer circumference of semi-spherical socket 14 is preferably formed with an annular recess 15 to define an annular shoulder (55, FIG. 2) for a purpose to be described below.

Abutment 40 is constructed to serve as a support for fixing the prosthesis 20 via the implant 11 to the bone. Prosthesis 20 (in this case an artificial tooth as indicated above) includes a generally cylindrical section 21 closed at its upper end 22 and formed with tapering sides 23 at its lower open end. Prosthesis 20 is coupled by abutment 40 and the ball-and-socket coupling 30 to implant 10 such as to enable the abutment to be angulated to its optimum position with respect to the implant before the abutment is fixed, and the prosthesis applied to the abutment.

The ball-and-socket coupling 30 includes ball 31 received within semi-spherical socket 14 formed at the upper end of implant 10. Ball 31 is formed with a central through-going bore 32 axially aligned with bore 12 of implant 10 in the normal upright position of abutment 40. Bore 32 is threaded, as shown at 33, for threadedly receiving fixation pin 41, to thereby couple abutment 40 to ball 30.

Fixation screw 41 of abutment 40 is formed with threads 41a at one end, threaded into bore 32 of ball 31. The opposite end of fixation screw 41 includes an enlarged head 42 formed with a non-circular (e.g., polygonal) recess or socket 43 to facilitate threading the screw into bore 32. An intermediate portion of fixation screw 40 is of reduced diameter to define an annular shoulder 44.

In addition to fixation screw 41, abutment 40 further includes: a sleeve 51 formed with an internal annular shoulder 52 engageable with the underside of the enlarged head 42 of fixation screw 41; a collar 53 engageable with annular shoulder 44 of the mid-portion of fixation screw 41; and an insert 54 between the undersurface of collar 53 and ball 31. The undersurface of collar 53 is formed with a spherical surface 53a complementary to that of ball 31. The two opposed faces of insert 54 are complementary to the spherical surface 53a of collar 53, and the portion of ball 31 which it contacts. As shown particularly in FIGS. 2 and 4, insert 54 is formed with the previously mentioned annular recess 55 about its outer circumference engageable with annular shoulder 15 of implant 10 to limit the pivotal movement of the ball-and-socket coupling 30.

The internal elements within abutment 40 further include a cover 56 overlying the enlarged head 42 of fixation screw 41.

As mentioned earlier and as also seen particularly in FIGS. 2 and 4, the internal elements within abutment 40 further include an annular shock absorber 60 interposed between annular shoulder 52 of sleeve 51, and the outer face 53b of collar 53. Shocks and other stresses applied to abutment 40 are absorbed by shock absorber 60 and are distributed by it and collar 53 before transmission by ball 31 and implant 10 to the bone carrying the implant.

It will thus be seen that after the implant system illustrated in FIGS. 1–4 has been implanted into the bone and before the prosthesis 20 has been applied, fixation screw 41 of abutment 40 may be pivoted, via ball-and-socket assembly 30, to optimize the angulation of the abutment with respect to the implant. When the abutment angulation has been optimized, the position of the abutment may then be fixed in any suitable manner, e.g., by an adhesive or by welding; and the prosthetic device 20 may then be applied in the conventional manner.

Preferably (not necessarily) the contacting surfaces between the semi-spherical socket 14 and ball 31 are made uneven, e.g., by providing one with dimples or dentents 34 and the other with projections 35. In this manner, the temporary positioning of abutment 40 may be facilitated, and the permanent fixing of the abutment in this position may be enhanced by adhesive or welding before fixing the prosthesis to the abutment.

It will also be seen that the shock absorber 60, interposed between annular shoulder 52 of sleeve 51 and the upper surface 53b of collar 53, absorbs shocks and distributes occlusal stress to the bone/implant interface more evenly than rigid (e.g., metal-to-metal) implant components, as in the prior art.

The Embodiment of FIGS. 5–8

FIGS. 5–8 illustrate an implant very similar to that of FIGS. 1–4, but omitting the prosthesis 20 and the shock absorber 60. Most of the remaining elements in the implant of FIGS. 5–8 are of basically the same structure, and operate in substantially the same manner, as described above with respect to FIGS. 1–4; therefore, in order to facilitate understanding, the corresponding elements have been identified by the same reference numerals, whereas the new or modified elements are identified by reference numerals beginning with "100".

Thus, the implant of FIGS. 5–8 omits the shock absorber 60 and the collar 53, of FIGS. 1–4; therefore the following additional changes have been made: First, the fixation screw, therein designated 141, is of shorter length than fixation screw 41 in FIGS. 1–4. In addition, sleeve 151, formed with an internal annular shoulder 152 engageable with the underside of the enlarged head of fixation screw 141, is also of shorter length, and its inner surface is of semi-spherical configuration as shown at 152a. As in FIGS. 1–4, the outer end of sleeve 151 is closed by cover 56.

Thus, while the implant illustrated in FIGS. 4–8 omits the shock absorber (60), and its collar (53), it retains the ball-and-socket mounting 30 between the implant 10 and abutment 140, to permit optimum angulation of the abutment with respect to the implant after the implant has been implanted into the bone.

Figure 9:
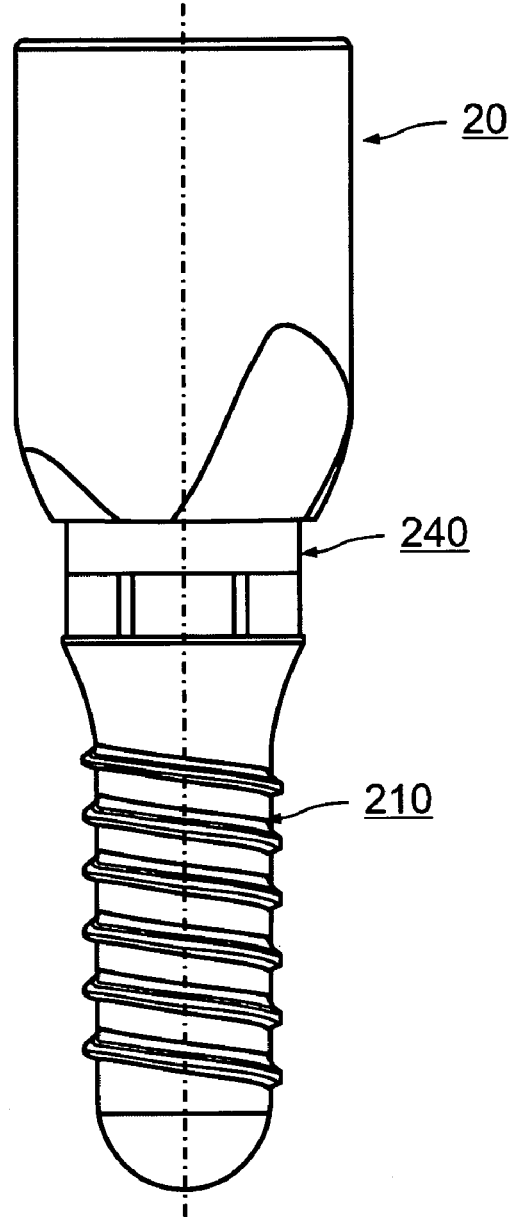
FIGS. 9 and 10 are views, corresponding to those of FIGS. 1 and 2, respectively, of a further implant system constructed in accordance with the present invention.
Figure 10:
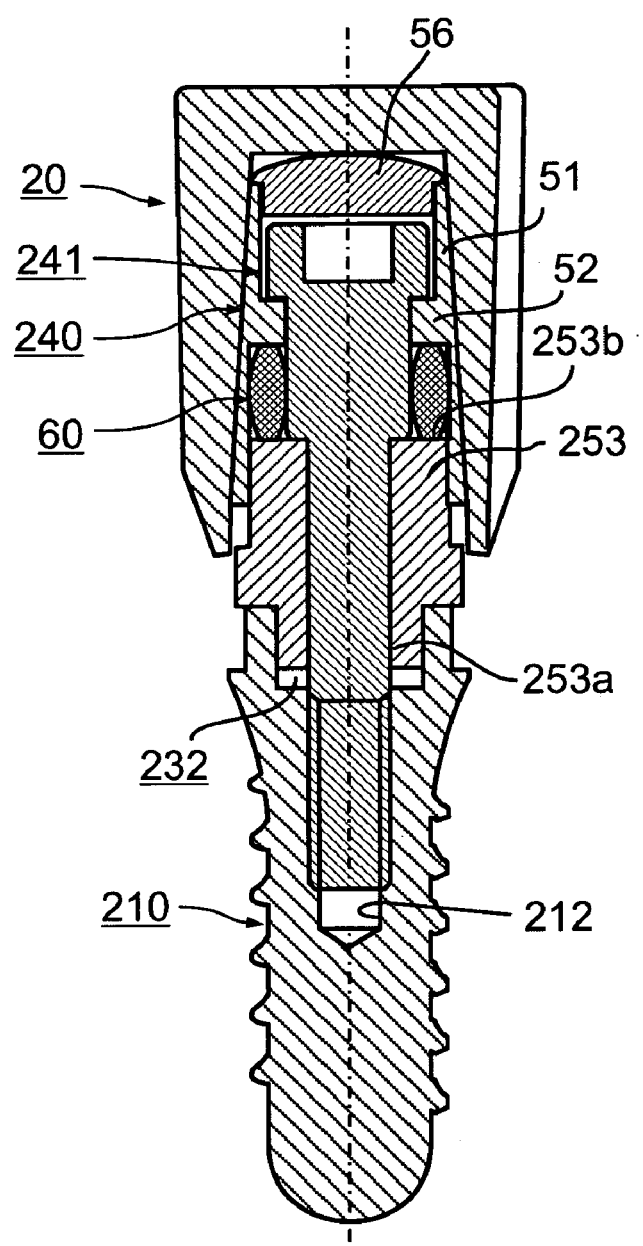

The Embodiment of FIGS. 9 and 10

FIGS. 9 and 10 illustrate an implant system, also similar to that of FIGS. 1–4, except that the ball-and-socket mounting 30 has been omitted. Again, to facilitate understanding, those elements generally corresponding to the elements described above with respect to FIGS. 1–4 are identified by the same reference numerals, whereas the new or modified elements are identified by reference numerals beginning with "200".

Thus, as seen particularly in FIG. 10, fixation screw 241 is elongated such that it extends into the threaded bore of the implant, therein designated 212 of implant 210, so as to be directly mounted to the implant. In addition, the implant 210 is formed with a socket 232 which is not semi-spherical, but rather is of a cylindrical configuration, for receiving an extension 253a of collar 253. As further shown in FIG. 10, the implant system also includes the annular shock absorber 60 interposed between the opposite face 253b of collar 253 and annular shoulder 52 formed in sleeve 51.

Accordingly, while the implant system illustrated in FIGS. 9 and 10 does not include the ball-and-socket mounting 30 of the two previously described embodiments, it does include the shock absorber 60, and thereby imparts to the implant system the ability to absorb shocks and distribute occlusal stress to the bone implant interface more evenly than e.g., metal-to-metal implant components.

While the invention has been described with respect to several preferred embodiments, it will be appreciated that these are set forth merely for purposes of example, and that many other variations, modifications and applications of the invention may be made.

What is claimed is:

1. An implant system, comprising:
   an implant constructed for implanting into a bone;
   an abutment constructed to serve as a support for fixing a prosthesis to the bone;
   and a pivotal coupling between said implant and said abutment to permit, after the implant has been implanted into the bone, precise angulation in all directions of the abutment with respect to the implant before the abutment is fixed at the desired precise angulation with respect to the implant;
   said pivotal coupling including a ball carried by said abutment, and a socket formed in said implant;
   said ball being formed with a threaded bore, and said abutment comprising a fixation screw having one end threaded into said bore;
   said fixation screw including an enlarged head, and said abutment further including a sleeve formed with an inner annular shoulder engaging said enlarged head of the fixation screw;
   said fixation screw being formed with an annular shoulder between its threaded end and enlarged head;
   said abutment further including a collar formed with a bore for receiving said threaded end of the fixation screw and engageable at its outer end with said annular shoulder of the fixation screw;
   said collar being formed at its inner end with a spherical surface complementary to that of said ball.

2. The implant system according to claim 1, wherein said pivotal coupling includes complementary shaped contacting surfaces which are uneven to temporarily hold the ball-and-socket coupling in a desired pivoted position before permanently fixing them in such position.

3. The implant system according to claim 1, wherein said pivotal coupling is fixed in a desired pivotal position by an adhesive or by welding.

4. The implant system according to claim 1, wherein said abutment further includes a cover closing the outer end of said sleeve.

5. The implant system according to claim 1, wherein said abutment further includes an insert between, and complementary to, said spherical surfaces of said collar and said ball; said insert being formed with an annular recess about its outer circumference limiting against an annular shoulder formed on the outer circumference of said implant to limit the angulation of said abutment with respect to said implant.

6. The implant system according to claim 1, wherein said implant system further comprises an annular shock absorber enclosing said fixation screw and engageable on its opposite sides by said collar and said annular shoulder of the sleeve.

7. The implant system according to claim 1, wherein said fixation screw includes an enlarged head at said opposite end engaged by an inner annular shoulder formed in said abutment for fixing said fixation screw within said abutment.

8. The implant system according to claim 7, wherein said abutment is formed at its inner end with a spherical surface complementary to that of said ball.

9. The implant system according to claim 8, wherein said abutment further comprises an insert between, and complementary to, said spherical surfaces of said abutment and said ball; said insert being formed with an annular recess about its outer circumference limiting against an annular shoulder formed on the outer circumference of said implant to limit the angulation of said abutment with respect to said implant.

10. An implant system, comprising:
    an implant constructed for implanting into a bone;
    an abutment constructed to serve as a support for fixing a prosthesis to the bone;
    and a shock absorber between said abutment and implant;
    said implant being formed with a cylindrical socket and a threaded bore;
    said abutment including a fixation screw having one end threaded into said bore and an opposite end enclosed by said shock absorber;
    said fixation screw including an enlarged head at said opposite end fixed within said abutment by a sleeve formed with an inner annular shoulder engaging said enlarged head;
    said fixation screw being formed with an annular shoulder between its threaded end and enlarged head;
    said abutment further including a collar formed with a bore for receiving said threaded end of the fixation screw;
    said collar being engageable at its outer end with said annular shoulder of the fixation screw for fixing it within said abutment and including an extension at its opposite end receivable within said socket of said implant and.

11. The implant system according to claim 10, wherein said abutment further includes a cover closing the outer end of said sleeve.

* * * * *